Figure 1:
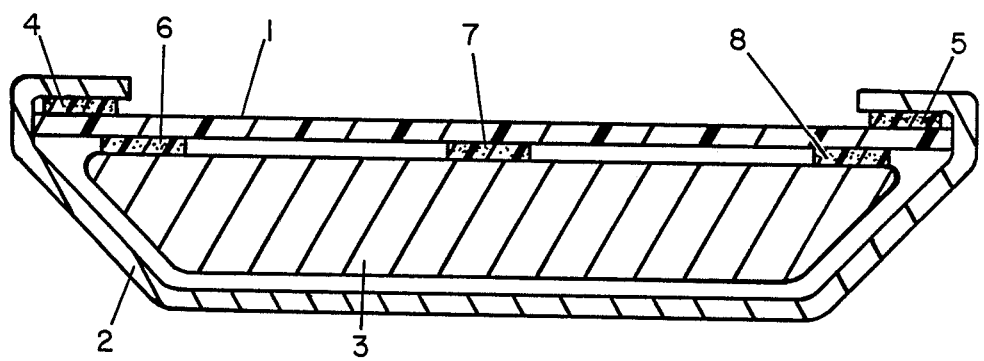

United States Patent [19]

Martini et al.

[11] Patent Number: 4,826,493
[45] Date of Patent: May 2, 1989

[54] SHEETS MATERIALS OF HB POLYMERS

[75] Inventors: Francesco Martini, Milan; Luigi Perazzo, Cuneo; Paolo Vietto, Milan, all of Italy

[73] Assignee: W. R. Grace & Co.-Conn., Duncan, S.C.

[21] Appl. No.: 85,037

[22] Filed: Aug. 13, 1987

Related U.S. Application Data

[62] Division of Ser. No. 939,375, Dec. 8, 1986.

[30] Foreign Application Priority Data

| Dec. 9, 1985 | [GB] | United Kingdom | 8530324 |
| Dec. 9, 1985 | [GB] | United Kingdom | 8530325 |
| Dec. 9, 1985 | [GB] | United Kingdom | 8530326 |
| Dec. 9, 1985 | [GB] | United Kingdom | 8530327 |
| Dec. 9, 1985 | [GB] | United Kingdom | 8530328 |
| Dec. 9, 1985 | [GB] | United Kingdom | 8530329 |

[51] Int. Cl.⁴ .................. A61M 1/00; B32B 27/08; C08J 5/18
[52] U.S. Cl. .................. 604/327; 428/332; 428/516; 428/518; 428/507; 604/333; 604/378; 264/514
[58] Field of Search .............. 428/520, 516, 518, 332; 604/333, 378, 327

[56] References Cited

U.S. PATENT DOCUMENTS

| 3,322,870 | 5/1967 | Sacks . | |
| 3,337,665 | 8/1967 | Underwood . | |
| 3,880,691 | 4/1975 | Pannenbecker . | |
| 4,019,505 | 4/1977 | Wartman | 128/90 |
| 4,048,428 | 9/1977 | Baird . | |
| 4,140,741 | 2/1979 | Lafferty . | |
| 4,289,727 | 9/1981 | Herrington . | |
| 4,333,464 | 6/1982 | Nakano | 428/516 X |
| 4,360,488 | 11/1982 | Barham . | |
| 4,372,311 | 2/1983 | Potts | 128/287 |
| 4,379,117 | 4/1983 | Baird . | |
| 4,391,766 | 7/1983 | Barham . | |
| 4,427,614 | 1/1984 | Barham . | |
| 4,537,738 | 8/1985 | Holmes . | |
| 4,620,999 | 11/1986 | Holmes | 428/520 X |

FOREIGN PATENT DOCUMENTS

| 0052460 | 5/1982 | European Pat. Off. . |
| 0078609 | 5/1983 | European Pat. Off. . |
| 103942 | 3/1984 | European Pat. Off. . |
| 0104731 | 4/1984 | European Pat. Off. . |

Primary Examiner—P. C. Ives
Attorney, Agent, or Firm—John J. Toney; William D. Lee, Jr.; Jennifer L. Skord

[57] ABSTRACT

HB polymers, such as copolymers of hydroxy butyric acid and hydroxy valeric acid, are provided as melt extruded films having a thickness of 5 to 200 μm. Sheet materials may consist of such a film or the film may be laminated with other films to increase strength or impermeability. The films are best made by co-extrusion with a thermoplastic that is substantially non-tacky upon solidification. The sheet materials are of particular value as diaper backsheets and ostomy bags. They may include a layer of non-woven material.

10 Claims, 2 Drawing Sheets

SHEETS MATERIALS OF HB POLYMERS

This is a divisional application of application Ser. No. 939,375, filed on Dec. 8, 1986.

This invention relates to novel products of polyesters such as hydroxy butyric acid homopolymers and copolymers with hydroxy valeric acid (referred to below as HB polymers) and to methods of making these products.

HB polymers have been known for at least 20 years. See U.S. Pat. No. 3,275,610. They are generally made biologically and they have the great advantage that they are biodegradable. This is of particular value with the increasing concern throughout the last decade or more about environmental pollution due to non-biodegradable polymeric products. Because of their environmental attractiveness they are therefore of great commercial potential importance. This is reflected by the very large number of publications in the last decade about their production and uses.

Environmental problems arise at present particularly with packaging films in that the environment is increasingly contaminated with plastic bags and plastic sheets that do not degrade, or degrade only very slowly. It would therefore have been expected that HB polymers would have been formulated as packaging films but, despite the enormous amount of work that has been done on them, this has not previously proved possible.

In U.S. Pat. No. 3,275,610 the HB polymer is produced biologically and is then purified by a purification process involving dissolution in a solvent, followed by evaporation of the solvent to produce a film of the polymer. The solvent-cast film was described as a "milky white pliable" film There have been many other references in the literature to films of HB polymers. Their production has, prior to the invention, always involved solvent casting, as above, and/or calendaring a coarse sheet or article. For instance in EP No. 0058480 HB polymer gel is oriented uniaxially or biaxially by cold rolling or drawing at temperatures preferably below 160° C. to give tough films, fibres or other shaped articles. The properties of solvent cast and/or cold calendared thin films are not commercially satisfactory in that the films are too brittle for packaging or many other uses.

Some of the literature on HB polymers does describe the production of films by a multi-stage process that includes, as an early stage, a melt extrusion step. However the melt extrusion step does not itself form the desired film but instead merely reduces the HB polymer composition to a form that can then be processed into a film, e.g., by cold calendaring. For instance in U.S. Pat. No. 4,427,614 a relatively coarse article was reduced in thickness by cold processing. Thus in example 1 plaques were made by compression moulding and were then rolled at room temperature to thicknesses ranging from 1.3 mm down to 400 microns. In example 4 a ribbon was made by melt extrusion through a 1.5 mm slot dye and was then cold calendared down to 450 microns. In example 11 a sheet 1 mm thick was made by solution casting and was then compressed and cold calendared to give an oriented film 25 $\mu$m thick.

Other references to melt extrusion include melt extrusion of a 4 mm diameter lace of HB polymer composition in example 11 of EP 0052946 and extrusion through an orifice of diameter 1.585 mm to form a mono-filament, followed by drawing of this filament, in EP No. 0104731. That process involves conditioning the extruded filament in a water bath before drawing and the patent notes that, although satisfactory drawing could be achieved with an 8 second conditioning time, satisfactory drawing could not be achieved when the time was only 5 seconds because the polymer was sticky. This reference is directed to a vital characteristic of HB polymers, namely that they remain sticky for a substantial time after their temperature has dropped below their melting point.

For this and other reasons it has so far proved impossible to produce thin films of HB polymers and instead their use is restricted to articles that can be made relatively coarse and as performance-improving additives in other polymeric compositions, e.g., as in EP No. 0052460. In particular it has been impossible to utilise HB polymers as a partial or complete replacement for the non-biodegradable polymers (for instance polypropylene and polyvinylidene chloride) from which most modern films are produced. If the biodegradable polymers are to replace these non-degradable polymer films it will be essential to be able to convert the biodegradable polymers into thin, coherent and flexible films by a method that can be operated reliably at high speed for prolonged periods. Despite two decades of research into these polymers, this objective has not previously been attained.

Although many synthetic polymeric materials can be reliably manufactured at high speed they do tend to suffer from deficiencies as regards their permeability properties.

Important physical properties of films are permeability to oxygen and permeability to moisture vapour. Existing films fall into three main classes. First, films such as polyvinylidene chloride have low permeability to oxygen and to moisture vapour. Second, films such as polyethylene and polypropylene have low permeability to moisture vapour but high permeability to oxygen. Third, films such as nylon and plasticised PVC and acrylonitrile have low permeability to oxygen but rather high permeability to water vapour and, in particular, the oxygen permeability increases as the humidity increases.

It would be desirable to provide a film in which the oxygen permeability is satisfactorily low and is substantially unaffected by its humidity whilst the moisture vapour permeability is sufficiently high that the film is comfortable when in contact with the body. Thus the film breathes. The only other synthetic films that have this breathing property are microperforated film, which is liable to permit leakage of liquid and has a very high oxygen permeability, and plasticised PVC, which is stretchable and liable to be toxic if held against the body for prolonged periods.

Products in which an impermeable and preferably biodegradable film would appear to have great value include products such as ostomy bags and diaper backsheets. The manufacture of such products in practice necessitates melt sealing the impermeable sheet to an adjacent surface, which can be of a similar sheet or of a different material. The melt sealing is best effected by RF welding. Unfortunately existing impermeable materials, such as polyvinylidene chloride, are not suitable for melt sealing and have to be provided with an additional melt sealing layer. It would be desirable to provide an impermeable film that did not necessitate this additional layer.

There are many instances where it is desirable to provide an article that is impermeable and that has additional physical characteristics, such as strength or softness, that cannot conveniently be achieved by a single ply of a water-impermeable film. In U.S. Pat. No. 4,372,311 a coating of HB polymer is applied on to a substrate and in GB No. 2,083,762 a coating of polyvinylidene chloride or other material is applied on to a substrate. However the amount of deposited polymer is always low and tends to be variable with the result that the coated substrate is usually not sufficiently impermeable. It would therefore be desirable to be able to provide a laminate of a film of HB polymer, having the desired impermeability and other properties, with a film or other sheet material imparting desired other properties to the laminate.

One object of the invention therefore is to provide improved films of HB polymer compositions, and improved ways of making such films.

Another object of the invention is to provide films of HB polymer compositions that have particularly beneficial physical properties, especially oxygen impermeability and moisture permeability.

Another object of the invention is to provide films that are impermeable and that can be melt bonded without the need for an intervening adhesion layer.

Another object of the invention is to provide laminates, and articles formed of such laminates.

We have now surprisingly found that it is possible to make a film of HB polymer compositions less than about 200 μm thick by melt extrusion and that such films, in contrast to films made by solution casting or cold calendaring, have much improved physical properties. In particular we have surprisingly found that these melt extruded films can have very desirable oxygen impermeability and moisture permeability, can be melt sealed without the need of an adhesion layer, can be laminated to other layers and can have satisfactory optical properties even when the polymer composition includes substantial quantities of cellular debris (thereby eliminating the need for extensive purification of the composition). Films according to the invention can be very flexible, especially when a plasticiser is incorporated.

In the invention a film of HB polymer composition is provided that is less than about 200 μm thick and that has been made by melt extrusion.

In this specification we use the term "HB polymer" to denote a biodegradable polymer formed of recurring units of which at least 50% molar, and preferably 100% molar, are units of formula 1

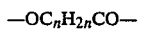

where n is 3, 4 or 5. Preferably the group $C_nH_{2n}$ has the formula

where m is 1, 2 or 3 and preferably all the groups of Formula I have m equals 1 or 2. For instance all the groups may have m equals 1 (polyhydroxy butyric acid) or at least 50% molar of the groups may have m equals 1 with the remainder of the groups having m equals 2 (polyhydroxy butyric-hydroxy valeric acid).

Recurring units other than those of Formula 1 and which are in the polymer are generally units of other hydroxy carboxylic acids of the general Formula 2

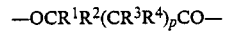

where p is zero or an integer and $R^1$, $R^2$, $R^3$ and $R^4$ may each be hydrogen, hydrocarbon (e.g., alkyl, aryl, alkaryl or aralkyl), halo substituted hydrocarbon, hydroxy substituted hydrocarbon, hydroxyl or halogen, provided that the values of $R^1$, $R^2$, $R^3$, $R^4$ and p are not such that the unit of Formula 2 is a unit of Formula 1.

Particularly preferred HB polymers are hydroxy butyric acid homopolymers and, most preferably, copolymers with hydroxy valeric acid. The amount of hydroxy valeric acid units in the copolymer can be up to about 50% molar and is usually at least about 5% molar. For many purposes amounts of from about 10 to about 30% molar are satisfactory but in some instances amounts of around 30% molar are best, for instance 20 to 40% molar.

The HB polymer is preferably made by biosynthesis for instance as described in U.S. Pat. No. 4,477,654. It may be purified by various methods as described in, for instance, EP Nos. 14490, 15123 and 58480. However satisfactory films for many purposes can be obtained even though the composition is contaminated with cellular debris and other by-products of fermentation, as described in more detail below, and so rigorous purification methods may not be required.

In this specification we use the term "HB polymer composition" to denote a composition of 50 to 100% by weight HB polymer with up to 50% by weight other materials. These other materials may include other polymers, cells or cell debris from the biosynthesis of the polymers, or additives included in the composition to improve its processing characteristics or its performance properties. Suitable additives include fillers, plasticisers, stabilisers and impact additives. Preferably the HB polymer is the only polymer in the composition and preferably at least 80% by weight of the composition is HB polymer. The composition therefore generally consists essentially of HB polymer, usually hydroxy butyric acid homopolymer or, preferably, copolymer with hydroxy valeric acid.

The film is generally at least about 5 and preferably at least about 10 μm thick. It is generally unnecessary for the film to be above about 150 μm thick and best results are generally obtained when the thickness is below about 100, and preferably below about 80 μm and most preferably below about 50 μm. Preferred films are often about 20 to 30 μm thick although for some purposes thicknesses of about 50 mm are preferred.

The films of the invention can have satisfactory flexibility, coherence and other physical properties and so, for the first time, it is possible to provide HB polymer compositions in the form of films having a thickness and other properties such that they can replace conventional non-biodegradable films.

A difficulty that arises when melt extruding HB polymer compositions is that the compositions remain tacky even after they have cooled to below their melting temperature (typically about 180° C. for a polyhydroxy butyrate homopolymer or about 120° C. for the preferred copolymers).

The invention includes a method of melt extruding an HB polymer composition against a molten layer, and preferably between a pair of molten layers, of a thermoplastic that is substantially non-tacky upon solidification, and stretching the extruded layers, generally after solidification. The provision of the substantially non-tacky thermoplastic material reduces the risk of the HB polymer composition film sticking to itself or to the apparatus.

A preferred method of the invention comprises co-extruding a laminated tube of a tubular layer of molten HB polymer composition and a tubular layer of molten thermoplastic that is substantially non-tacky on solidification. Generally the resultant laminated tube is cooled and is then inflated in order to stretch the film. The inflated tube may then be flattened. If it is desired for the film to be produced as a flat sheet the tube may subsequently be slit.

The general methods of co-extruding a tacky polymer as a tube with an inner tube, and possibly an outer tube, of less tacky material are described in U.S. Pat. Nos. 3,880,691 and 4,379,117 and the same general techniques and apparatus may be used as are illustrated and described in those patents which are hereby incorporated in their entirety by reference.

The said non-tacky thermoplastic is generally extruded as an internal layer of the laminated tube since it facilitates prevention of adhesion of facing surfaces of the laminated tube when that tube is collapsed, for instance prior to slitting. Often however adhesion of the extruded tube to external handling apparatus, for instance for drawing the film away from the extrusion orifice, is potentially a problem and to avoid this it is desirable to co-extrude the said non-tacky thermoplastic on the outside of the tubular layer. In the invention preferably the tubular layer has an inner layer of the said non-tacky thermoplastic, a central layer of the HB polymer composition and, preferably, an outer layer of the said non-tacky thermoplastic. Additional layers may be incorporated.

The non-tacky thermoplastic layer or layers may be present solely as sacrificial layers that are to be stripped from the HB layer after that layer has finally solidified or the non-tacky thermoplastic layer, or one of the layers, may remain permanently bonded to the HB polymer layer.

When the co-extruded non-tacky thermoplastic layer, or either or both of the layers, is to be sacrificial the material will be chosen such that the HB polymer composition tends to adhere strongly to that layer while the HB polymer composition is non-crystaline but will tend to become non-adherent as the HB composition crystalises. By appropriate choice of materials it is possible easily to separate the substantially non-tacky thermoplastic layer or layers from the HB polymer composition film after that has crystallised. The time necessary for crystallisation to occur will depend upon the ambient temperature and upon whether or not a crystallisation initiator is present in the composition. It may be necessary to allow the laminate to age for as long as 24 hours before delamination but it is often unnecessary to age for longer than 4 hours. Suitable nucleating agents that may be included to accelerate crystallisation include infusible inorganic or organic particulate materials such as talc and fusible organic materials that, upon cooling the polymer composition, will crystallise faster than the polymer, for instance benzoic acid.

The resultant film is generally substantially unoriented, at least compared to the highly oriented films obtained by the cold drawing techniques described in, for instance, example 11 of U.S. Pat. No. 4,427,614 and it is surprising that a melt extruded film that is substantially unoriented can have properties as satisfactory as the properties obtainable in the invention. However if greater degrees of orientation are required the film may be drawn further after it has crystallised.

Suitable materials that can be used as the substantially non-tacky thermoplastics include polyolefins, especially polyethylene, and ethylene vinyl acetate copolymers. Lower proportions of vinyl acetate, for instance 2 to 10%, are preferred when it is desired to be able to strip the ethylene vinyl acetate film quickly and easily from the HB polymer composition film but higher vinyl acetate contents, for instance 10 to 25%, are preferred when optimum inflation of the tube is required, for instance to produce very thin films.

Laminates according to the invention can be formed by calendaring an HB polymer composition film of the invention with another preformed film whilst providing an adhesive between the two layers. Preferably however the laminate is made by co-extrusion of the HB polymer composition film with suitable reinforcing or other film that will permanently adhere to it, even after crystallisation of the HB polymer composition film. The reinforcing film will then serve as the non-tacky thermoplastic layer. The reinforcing film may serve to reinforce the strength properties or to improve the permeability properties or to modify the HB film in any other suitable manner.

For some products it is preferred that substantially all material in the laminate other than the biodegradable film should be water soluble so that upon discharging the laminate into water the laminate either dissolves or degrades biologically.

A preferred water soluble film is polyvinyl alcohol. It is usually at least 5 and preferably at least 10 $\mu$m thick. It is generally less than 200, preferably less than 150 and most preferably less than 100 $\mu$m thick. Preferred thicknesses are 10 to 50 $\mu$m, especially 20 to 30 $\mu$m. Another suitable water soluble film is polyethylene oxide but for cost reasons it is desirable to keep its thickness below 20 $\mu$m, typically 5 to 15 $\mu$m.

A preferred laminate comprises HB polymer composition film coextruded with polyvinyl alcohol film with a bonding layer of polyethylene oxide between the HB composition and polyvinyl alcohol. Sometimes it is desirable also to provide another bonding layer between the polyethylene oxide and the polyvinyl alcohol and a very thin layer of ethylene vinyl alcohol may be coextruded with the other films for this purpose.

However for other products the incorporation of a water insoluble reinforcing or intermediate film is satisfactory, especially if that insoluble film is sufficiently pliable that it is unlikely to cause drain blockage. For instance any insoluble and non-biodegradable film components would preferably have a total thickness of not more than 50 $\mu$m and when, as is preferred, one of the co-extruded films is polyvinylidene chloride its thickness is preferably not more than 15 or 20 $\mu$m. It is particularly preferred that the thickness of any insoluble and non-degradable film should be below 5 $\mu$m so as to facilitate its physical comminution and destruction during normal water treatment operations.

The laminate may consist solely of the biodegradable film and the adherent reinforcing film but it is often desirable to coextrude one or more intermediate films between the biodegradable film and the reinforcing film. These intermediate films are generally present to improve the adhesion between the biodegradable and reinforcing films. Additionally there may be one or more films over the surface of the reinforcing film.

Instead of co-extruding the PHB composition film and the reinforcing film or films it is sometimes more convenient to form the HB polymer composition film and then to laminate it to the reinforcing film or films. For this purpose the HB polymer composition film may have a thickness of, for instance, about 20 to about 80 μm, often 30 to 60 μm and permanent adhesion of this film with the reinforcing film may be achieved by provision of a laminating adhesive between the films.

Suitable adhesives for the lamination of films are well known and include polyurethane adhesives, especially two-component adhesives, such as the product sold by Morton Thiokol under the trade name Adcote 710 A & C. The amount of laminating adhesive is usually in the range about 1 to about 15 g/m$^2$, preferably around 5 g/m$^2$.

The reinforcing film can be, for instance, polyethylene typically of 10 to 50 and preferably about 30 μm thickness but if impermeability to oxygen is to be reduced then the reinforcing film preferably comprises an impermeable film such as polyvinylidene chloride, optionally laminated (often on the surface distant from the HB composition) with ethylene vinyl acetate. The PVDC film typically is from 4 to 20 μm thick. It is particularly preferred to use a PVDC film of 4 to 15 μm that is co-extruded with an ethylene vinyl acetate film of 2-15 μm thickness that provides the other surface of the resultant laminate. An ethylene vinyl acetate film of 2-15 μm may also be co-extruded on the side of the PVDC layer adjacent to the HB composition film. Preferably the PVDC layer is 5-11 μm thick, the or each EVA layer is 3-10 μm thick and the co-extruded film 10-20 μm thick. The total laminate preferably has an oxygen permeability of below 150 cc/m$^2$.day.bar, generally below 100 and most preferably below 80. This laminate is especially suitable for the production of an ostomy bag, with the PVDC layer facing inwards, melt sealed around its edges.

Preferred laminates according to the invention comprise an HB composition layer that is plasticised by the inclusion in the HB composition of plasticiser generally in an amount of from about 5% to about 40% by weight of the HB polymer composition (including plasticiser). Typical amounts of plasticiser are from about 10 to about 35% by weight of the composition. Suitable plasticisers for use in the invention include sulphonamides, such as N-ethyl-o,p-toluene sulphonamide, and glutarates such as dialkyl diether glutarate having a molecular weight of about 450.

The inclusion of plasticiser increases the permeability of the film to oxygen but the lamination, either by co-extrusion or by an adhesive layer, with polyvinylidene chloride or other impermeable film results in the production of a flexible, soft, oxygen-impermeable laminate. This is very suitable for use as a diaper backsheet or an ostomy bag.

Polyvinylidene chloride films used in the invention for reducing permeability may be any of the appropriate commercially available vinylidene chloride homopolymers or vinyl chloride vinylidene chloride copolymer films that are commercially available as impermeable films.

Instead of or in addition to laminating the HB composition film of the invention to another film, it may be bonded to a non-woven fabric. The non-woven fabric is generally bonded to the film after the film has been stretched to its final dimensions and is solid. Bonding can be by fusion of the web to the film, for instance as a result of the provision of a very low melting layer over the film, in which event this layer may have been coextruded with the film. Preferably however the non-woven fabric is laminated with the film by calendaring the film with the non-woven fabric with a liquid adhesive composition between the fabric and the film. Suitable adhesives for this purpose are usually water soluble or decomposable adhesives, for instance polyethylene oxide, polyvinylpyrrolidone/vinylpyrrolidone vinylacetate copolymers, hydroxylated derivatives of polyacrylic acids, polyesters, produced by the reaction of:

(a) isophthalic and terephthalic acids, sulphonated acids, one or more glycols, suitabley neutralised with sodium hydroxide.

(b) isophthalic and terephthalic acids, maleic anhydride, one or more glycols, suitable neutralised with sodium hydroxide or ammonia.

(c) acrylic esters, acrylic acid, acetic esters of polyhydric alcohols.

The adhesive may be dispersed or dissolved in water or in an aqueous or anhydrous mixture of organic solvent, generally volatile alcohol, ketone or ester.

At least 50% and preferably at least 80%, and most preferably all, of the fibres in the non-woven fabric are cellulosic fibres in order that they will swell in water so as to rupture the fabric and facilitate degradation of it. Preferably they are staple fibres, as opposed to continuous filaments. The non-woven fabric can be needled but this is usually unnecessary. The fibres in the fabric are preferably bonded to one another by a water soluble or dispersable bonding agent so that this bonding agent dissolves or disperses into water when the laminate is immersed in water. Acrylic bonding agents are often suitable. The agent is preferably water soluble or dispersible.

The fabric may have been made in conventional manner, for instance by forming a web of the fibres and then impregnating this web with the chosen bonding agent. The weight of fibres is generally from 10 to 70 g/m$^2$ and the weight of bonding agent is generally from 2 to 50 dry weight g/m$^2$. The dry weight of the adhesive used to bond the fabric to the film is generally from 2 to 10 g/m$^2$.

The laminate of the non-woven fabric with the HB polymer film (and optionally other films) can provide an article combining the permeability and biodegradable properties of the film with the softness of the non-woven fabric. The non-woven fabric is prferably arranged on the surface of the film distant from the surface that is to contact liquids and thus, for instance, an ostomy bag according to the invention may have an inner layer of the film and an outer layer of the non-woven fabric.

The permeability properties of the HB polymer composition films of the invention will be affected by, for instance, the thickness of the films and the amount of plasticiser or other material that is included in the HB polymer composition but it is easily possible in the invention (especially when the amount of plasticiser is low, e.g., below 10% and preferably below 5% and preferably substantially absent) to produce films that have a very low permeability to oxygen. Thus it is easily possible to produce films that have oxygen permeability of 10 to 200 (preferably 80 to 20) cc/m$^2$.day.bar (measured at 23° C. and 0% R.H.).

It is also easily possible in the invention to produce films of the HB polymer composition that have a satisfactorily high moisture vapour transmission. Thus it is possible to make films that have moisture vapour transmission (MVT) of at least 30 (preferably 40 to 150) g/m².day measured at 38° C. and 100% ΔRH.

The quoted values are especially suitable for films of 25 μm thickness.

The permeably to oxygen and the moisture vapor transmission are is substantially inversely proportional to thickness and suitable values, per 1 μm thickness, are below 2000 and above 2000, respectively, per μm.

Thus in the invention it is possible to provide films in which the oxygen permeability is satisfactorily low and is substantially unaffected by its humidity whilst the moisture vapour permeability is sufficiently high that the film is comfortable when in contact with the body. Thus the film breathes. The only other synthetic films that have this breathing property are microperforated film, which is liable to permit leakage of liquid and has a very high oxygen permeability, and plasticised PVC, which is stretchable and liable to be toxic if held against the body for prolonged periods.

The extruded HB films of the invention can have good gloss and low haze. The haze is generally below 20%, preferably 10 to 20%, measured by ASTM D-1003 using a Gardner haze meter. The gloss of films in the invention is usually 80 to 110 or 120 measured by ASTM D-2457 using a sheen gloss meter and an incidence angle of 60°.

When films are made from HB polymer compositions consisting essentially of 100% HB polymer (for instance including up to about 2% impurities) it is observed that the films have good optical properties, having low haze (below 10%) and high gloss (above 95 or 100). It would be expected that the inclusion of cellular debris and other impurities would dramatically decrease the optical properties of the films. We have surprisingly found that this is not the case and that instead, it is possible to form melt extruded films generally of below 50 μm that have satisfactory optical properties from HB polymer compositions containing for instance 5 to 20%, usually 5 to 15%, impurities remaining from the fermentation of the films. These impurities are generally cell debris. The haze is generally below 20%, usually 10 to 20%, and the gloss can often be at least 88, e.g., 88 to 98.

Thus good films can be made even though the polymer composition has not been subjected to the expensive purification steps that are required for making the purest polymer compositions.

Ostomy bags at present are generally made from a laminate of polyvinylidene chloride (to give impermeability) with a surface layer of ethylene vinyl acetate (to give softness and heat sealability). Polyvinylidene chloride cannot satisfactorily be melt sealed. We have surprisingly found that the melt extruded HB composition films of the invention can be melt sealed and so it is not necessary to laminate them with a melt sealing surface layer, such as ethylene vinyl acetate. Thus an ostomy bag, diaper backsheet or other article can be made by laying the face of a melt extruded film of HB polymer composition against a surface and melt sealing it against the surface. The surface is generally the face of melt extruded film of HB polymer composition and thus an ostomy bag may be made by folding such a film upon itself and melt sealing it around the edges. Instead of folding one film upon itself, two separate films may be laid against each other, with the HB polymer composition layers facing each other. Other surfaces to which the film may be melt sealed include articles that are to be secured into the film, e.g., the fitting of an ostomy bag.

The melt sealing may be by impulse heating or, preferably, RF welding. This comprises the application of a high frequency electromagnetic field between a pair of metallic jaws that clamp the layers that are to be welded. Parameters that influence the process performances are frequency, sealing time and pressure on the jaws. In the invention preferred frequencies are 27 to 70 MHz; preferred sealing times are 0.5 to 5 seconds; preferred pressures are 0.5 to 10 bars.

The invention is illustrated in the accompanying drawings, in which

Figure 2:
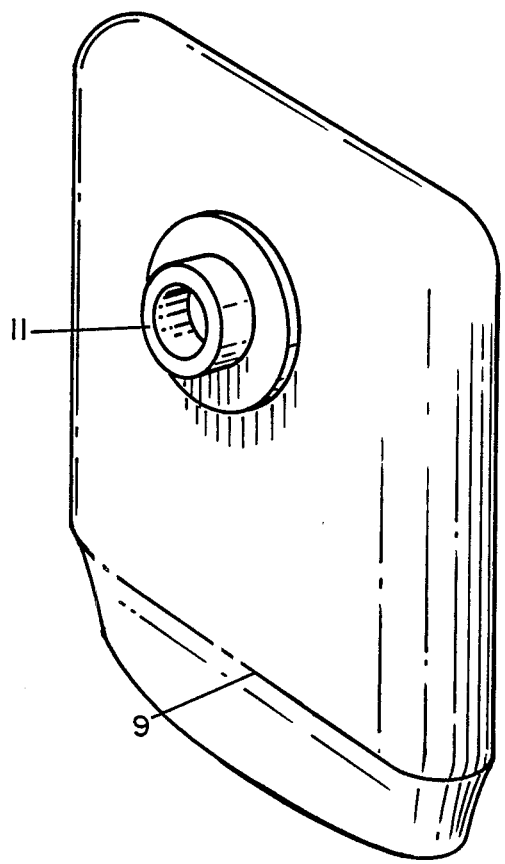
Figure 3:
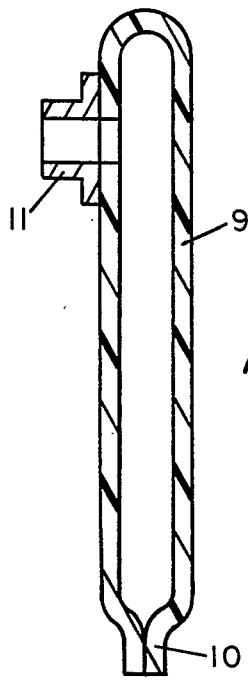
Figure 4:
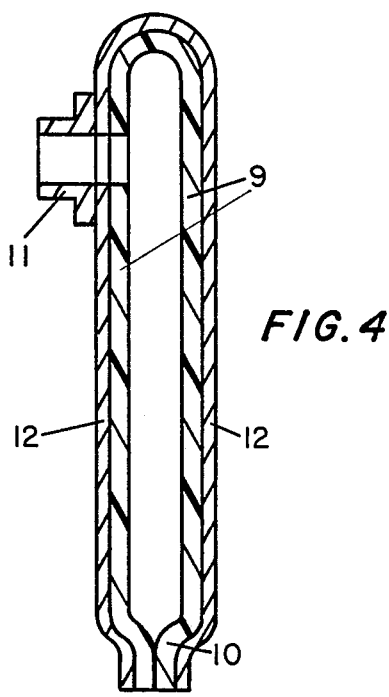

FIG. 1 is a section through a diaper
FIG. 2 is a perspective view of an ostomy bag
FIG. 3 is a cross section through the bag, and
FIG. 4 is a similar cross section through a different bag.

The diaper in FIG. 1 comprises a backsheet 1 of a melt extruded film of HB polymer composition, a permeable, non-woven, top sheet 2 and an absorbent pad 3 of cellulosic or other suitable material. The backsheet 1 is melt sealed to the top sheet along each side, and across the ends, as shown at 4 and 5, and is melt sealed to the absorbent pad along three longitudinal strips, as shown at 6, 7 and 8.

The ostomy bag in FIGS. 2 and 3 comprises a film 9 formed into a pouch and melt sealed around its facing edges 10 and melt sealed to an ostomy fitting 11.

In FIG. 4 the film 9 is laminated to an outer layer 12. In one embodiment of the invention this outer layer 12 may be a water-degradable non-woven fabric. In another embodiment it may be a reinforcing film and layers 9 and 12 may be reversed so that layer 12 is inside layer 9 and it may then comprise, for instance, a layer of polyvinylidene chloride film, for instance coated on the inner surface with EVA so as to promote adhesion of the facing surfaces of the layer 12.

Instead of forming the bags shown in FIGS. 3 and 4 from a single sheet that is folded upon itself, they may be formed from two separate sheets that may be bonded to one another around their entire periphery.

The following are some examples of the invention.

EXAMPLE 1

A composition of about 98% of a copolymer of 83% hydroxy butyrate and 17% hydroxy valerate is extruded with ethylene vinyl acetate containing about 3% vinyl acetate as described in U.S. Pat. No. 4,379,117, especially FIG. 3. The extrusion dye had a diameter of about 100 mm and provided, at the point of extrusion, a tubular laminate of 0.9 mm EVA, 1.2 mm HB polymer and 0.9 mm EVA. The extrusion temperature was about 10° to 20° C. above the melting point of the composition. The tube was inflated to a diameter of about 400 mm so as to stretch it laterally fourfold and was stretched longitudinally by adjusting the take-off speed at up to 40 meters per minute, the resultant film thickness being about 25 μm. After ageing overnight the film was slit longitudinal and the EVA layers separated from the HB polymer composition layer. The resultant film was labelled A.

The process was repeated using a similarly pure composition but based on a copolymer of 78% hydroxy butyrate and 22% hydroxy valerate. The resultant film was labelled B.

The process was repeated but using a copolymer of 82% hydroxy butyrate and 18% hydroxy valerate in a composition containing about 10% cell debris. The film was labelled C.

Various physical properties of films A, B and C were recorded. As comparisons, the corresponding properties were recorded of film D, biaxially oriented polypropylene about 20 μm thick and of film E which is film D, perforated with holes about 0.4 mm diameter. The results are shown in the table below in which, for comparison, typical values for polyvinylidene chloride film, F, are shown.

| Code | | A | B | C | D | E | F |
|---|---|---|---|---|---|---|---|
| $O_2$ Transmission | | 130 | 145 | 140 | 1,650 | — | 5–50 |
| MVT | | 75 | 80 | 45 | 7–8 | 190–220 | 7.5 |
| Modulus | L | 19,000 | 11,000 | 22,000 | 30,000 | 22,500 | — |
| | T | 20,000 | 11,000 | 22,000 | 25,000 | 21,000 | — |
| TS | L | 300 | 290 | 250 | 2,600 | 1,150 | — |
| | T | 320 | 280 | 250 | 1,200 | 1,000 | — |
| Elongation % | L | 3 | 8 | 2 | 95 | 40 | — |
| | T | 3 | 9 | 3 | 75 | 35 | — |
| Haze % | | 8 | 10 | 14 | 2–3 | — | 4–5 |
| Gloss | | 110 | 95 | 92 | 140–145 | 110–120 | 100 |
| TPR | L | 0.4 | 1.2 | 0.4 | 2.5 | 12 | — |
| | T | 0.5 | 1.3 | 0.4 | 2.6 | 9 | — |

$O_2$ transmission is recorded in cc/25 μm.m$^2$.day, bar at 23° C.
MVT (moisture vapour transmission) is recorded in g/25 μm.m$^2$.day at 38° C.
Modulus and TS (tensile strength) are recorded in kg/cm$^2$.
TPR (tear propogation resistance) is recorded in g/μm.

The results demonstrate the excellent combination of oxygen and moisture vapour transmission properties of the films according to the invention (A, B and C) compared to the prior art films (D and F) and the prior art perforated film (E). The results also demonstrate the satisfactory haze and gloss values that are obtained despite the presence of substantial amounts of cell debris impurities (C).

Films A, B and C are suitable for use as the backsheet 1 in the diaper of FIG. 1 or the pouch 9 in the ostomy bags of FIGS. 2 to 4.

EXAMPLE 2

Films are produced by extrusion as in Example 1 of a composition of a blend of substantially pure HB polymer formed of 79 mole percent hydroxy butyric acid and 21 mole percent hydroxy valeric acid together with varying amounts of plasticiser. In Example 2a the plasticiser is N-ethyl-o,p-toluene sulphonamide (available from Monsanto under the trade name Santicizer 8) in an amount of 60 parts per 100 parts polymer. In Example 2b the plasticiser is a blend of 10 parts per 100 parts polymer of this sulphonamide and 10 parts per 100 parts polymer of a dialkyl diether glutarate of molecular weight about 450 available from C. P. Hall as Hall 7050. In Example 2a the film is extruded to a final thickness of about 40 μm and in Example 2b it is extruded to a thickness of about 50 μm.

EXAMPLE 3

The film of Example 2a is laminated with a 12 μm biaxially oriented polyvinylidene chloride film using a conventional two-component polyurethane adhesive supplied for laminating films, in particular 5 g/m$^2$ Adcote 710 A & C supplied by Morton Thiokol. The resultant laminate is very flexible and soft and could be utilised as a diaper backsheet or an ostomy bag as illustrated or described with reference to any of the accompanying drawings. The laminated film has an oxygen permeability of 50 cc/.m$^2$.day.bar at 23° C.

EXAMPLE 4

The film of Example 2b is laminated, using the same adhesive and the same general technique as in Example 3, with the polyvinylidene chloride surface of a laminate of 10 μm polyvinylidene chloride and 30 μm ethylene vinyl acetate containing 18% vinyl acetate (the material from Dupont under the trade name Elvax 3165), this laminate having been made by co-extrusion through a circular dye followed by hot blowing. The resultant laminate had an oxygen impermeability of 14 cc/m$^2$.day.bar and could be used as the backsheet in FIG. 1 or as the laminate in FIG. 4, with the HB polymer film either on the inside or the outside of the bag.

EXAMPLE 5

The film of Example 2b is laminated by the same general technique and using the same adhesive as is in Example 3 with a 30 μm film of polyethylene (containing 5% vinyl acetate).

EXAMPLE 6

The process of Example 4 can be repeated with different ethylene vinyl acetates having vinyl acetate contents ranging from 5 to 25% and mfi of 0.5 to 7 and can also be repeated using a laminate in which there is an ethylene vinyl acetate layer on the side of the polyvinylidene chloride facing the layer of HB polymer.

EXAMPLE 7

Coextrusion is conducted using method and apparatus as described in U.S. Pat. No. 4,379,117, especially FIG. 3, but modified to provide four films instead of three.

The materials that are extruded are, in sequence, polyvinyl alcohol, polyethylene oxide, HB polymer composition consisting of about 98% of a copolymer of 83% hydroxy butyrate and 17% hydroxy valerate, and ethylene vinyl acetate containing about 3% vinyl acetate. The extrusion dye has a diameter of about 100 mm and provides, at the point of extrusion, a tubular laminate of 0.6 mm polyvinyl alcohol, 0.3 mm polyethylene oxide, 1.2 mm HB polymer and 0.9 mm EVA. The extrusion temperature is 10 to 20%C. above the melting point of the highest melting component of the laminate, namely 140° C.

The tube is inflated to a width of about 400 mm so as to stretch it laterally fourfold and is stretched longitudinally by adjusting the take-off speed at up to 40 meters per minute. The resultant laminate consists of films of polyvinyl alcohol 13 μm thick, polyethylene oxide 6 μm thick and HB polymer composition about 25 μm thick. After ageing overnight the film is slit longitudinally and the EVA layer separated.

We claim:
1. In a sheet material comprising a film of hydroxy butyric acid polymer composition wherein the hydroxy butyric acid polymer is a biodegradable polymer formed of recurring units of which 50 to 100% molar are units of formula 1

$$-OC_nH_{2n}CO-$$

where n is 3, 4 or 5 and the hydroxy butyric acid polymer composition comprises 50 to 100% of the hydroxy butyric acid polymer and 0 to 50% diluent additive, wherein the improvement comprises that (a) the film is a film that has been made by melt extrusion to a thickness of 5 to 200 μm, that (b) the film of hydroxy butyric acid polymer composition has moisture vapor transmission of 30 to 200 g/25 um.m$^2$.day at 38° C. and has an oxygen transmission value of 10 to 200 cc/25 um.m$^2$.day.bar at 23° C., and that (c) the film of hydroxy butyric acid polymer composition is laminated with and bonded to a sheet material selected from non-woven fabrics, water soluble films and insoluble films.

2. A material according to claim 1 in which the hydroxy butyric acid polymer composition includes 5 to 40% plasticizer, the film of hydroxy butyric acid polymer composition is from 10 to 100 um thick, and the film is laminated to a water insoluble film selected from polyethylene, ethylene vinyl acetate copolymers, polyvinylidene chloride, and laminates comprising polyvinylidene chloride.

3. A material according to claim 2 in the form of an ostomy bag of diaper backsheet.

4. A material according to claim 1 comprising a laminate of the film of hydroxy butyric acid polymer composition with a film of polyvinyl alcohol.

5. A material according to claim 1 comprising a laminate of the film of hydroxy butyric acid polymer composition with a water-degradable non-woven fabric.

6. A material according to claim 5 in the form of an ostomy bag or diaper backsheet.

7. A material according to claim 1 comprising the said film of hydroxy butyric acid polymer composition melt sealed, without any intervening bonding layer, to a surface.

8. A material according to claim 7 in the form of a diaper or ostomy bag.

9. A material according to claim 1 comprising the said film of hydroxy butyric acid polymer composition melt sealed, without any intervening bonding layer, to a melt extruded film of hydroxy butyric acid polymer composition.

10. A material according to claim 9 in the form of a diaper or ostomy bag.

* * * * *